United States Patent

Subramanyam et al.

[11] Patent Number: 5,417,892
[45] Date of Patent: May 23, 1995

[54] ISETHIONATE ETHER SURFACTANT

[75] Inventors: Ravi Subramanyam, North Brunswick; Ben Gu, East Brunswick, both of N.J.

[73] Assignee: Colgate-Palmolive Company, Piscathaway, N.J.

[21] Appl. No.: 267,337

[22] Filed: Jun. 28, 1994

[51] Int. Cl.$^6$ .............. C11D 1/12; C07C 309/08; C07C 309/09

[52] U.S. Cl. .................. 252/554; 252/549; 252/555; 252/121; 562/110; 562/111; 562/112

[58] Field of Search ............ 562/103, 110, 111, 112; 252/554, 555, 121, 132, 107

[56] References Cited

U.S. PATENT DOCUMENTS

| | | | |
|---|---|---|---|
| 2,062,957 | 5/1931 | Baldwin et al. | 562/111 |
| 2,094,489 | 3/1932 | Hueter | 562/111 X |
| 2,535,678 | 2/1947 | Hollander et al. | 562/111 X |
| 3,082,249 | 3/1963 | Gaertner | 562/110 |
| 5,310,508 | 5/1994 | Subramanyam et al. | 252/549 |

FOREIGN PATENT DOCUMENTS 260110  11/1960  Australia .

*Primary Examiner*—Linda Skaling
*Assistant Examiner*—Margaret Einsmann
*Attorney, Agent, or Firm*—Martin B. Barancik; Robert C. Sullivan

[57] ABSTRACT

A compound of the formula $$ROCH_2CHOHCH_2O\ CH_2CH_2SO_3^-X^+$$

wherein R is alkyl, alkenyl of eight to twenty two carbon atoms or mixtures thereof inclusive and X is an alkali metal, alkaline earth metal, ammonium or substituted ammonium compound.

10 Claims, No Drawings

ISETHIONATE ETHER SURFACTANT

BACKGROUND OF THE INVENTION

New surfactants are continually being discovered for usage in compositions requiring surfactant activity. Of particular interest are surfactants for personal cleansing compositions, shampoos, body washes, shower gels, make up removal, cosmetics, laundry detergents, cleaning of hard surfaces in the bath and/or kitchen and the like. Various synthetic surfactants such as sodium cocoyl isethionate (SCI), alkyl glyceryl ether sulfonates (AGES), cocoylmonoglyceride sulfate (CMGS) and the like have become quite successful over the years of usage.

A new surfactant has now been discovered which will be useful in the above named consumer product areas, particularly in personal cleansing, shampoos, body washes and shower gels. It is characterized by relative simplicity in structure and a desirable mildness.

SUMMARY OF THE INVENTION

In accordance with the invention there is a compound of the formula.

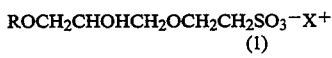

FIG. I (1)

wherein R is alkyl or alkenyl of eight to twenty two carbon atoms inclusive or mixtures thereof and X is an alkali metal, alkaline earth metal, ammonium or substituted ammonium compound.

DETAILED DESCRIPTION OF THE INVENTION

The R group in the compound is preferably 10 to 20 carbon atoms in length. Although branching can be present in the group it is preferred to be normal. Alkyl is preferred over an unsaturated, alkenyl, group. There can be up to 20 wt %, preferably up to 10 wt % alkenyl grouping present as a mixture with the alkyl as a further preferred mode.

With respect to the X grouping the alkali metal is preferably sodium or potassium, the alkaline earth metal is preferably magnesium or calcium. The ammonium type compounds are preferably the hydroxy substituted materials such as triethanolamine. Sodium, potassium, ammonium and triethanolamine are most preferred.

These compounds are made by well known synthetic methods such as the reaction of sodium isethionate (2) with the epoxide (3) or chlorohydrin (4) shown below preferably in the presence of suitable catalyst.

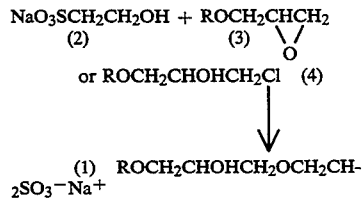

FIG. II

Suitable catalysts which can be employed include potassium hydroxide, sulfuric acid, stannic chloride, hydrated stannic chloride (5 H$_2$O) and the like. Generally the reaction is preferably performed at an elevated temperature for an extended period of time. Temperatures of from about 40° C. to the reflux and stability termination temperature of the system can be employed. Preferably the temperature is about 60° to 275° C. The time of the reaction is dependent upon the catalyst and the temperature; however times from several minutes to hours can be employed. Generally reaction times of about 15 minutes to twelve hours can be employed. Yields of (1) vary from about 2 to 13% depending upon the time of reaction and the catalyst employed.

A further reaction sequence to obtain (1) is through the reaction of the ethoxylated derivative of the bromo hydrin (5) with sodium sulfite (6) in water to obtain (1). The R grouping is as previously defined.

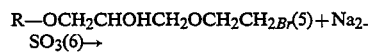

(1)

Compound (5) is prepared by reacting a glycidate with a 2-haloethanol using a boron trifluoride etheareate catalyst system at 55° C. for a two hour reaction time.

The novel compounds of the invention are useful in the above-mentioned surfactant applications in any of a variety of formulations such as solid and liquid and can take various forms such as a bar (personal or laundry), aqueous liquid, organic based liquid, mousse, gel and the like and can be combined with a soap, other synthetic surfactant, detergent extender, structural filler, colorant, preservative, fragrance, chelating agent, antibacterial agent, emollient and any other type of material found in applications of the nature described.

Examples of soaps or synthetic surfactants include as soaps the long chain (C$_{8-22}$) preferably C$_{10-20}$ alkyl and-/or alkenyl carboxylate salts. Typical synthetic surfactants include anionic, cationic and nonionic materials such as phosphates, sulfates, sulfonates, sulfosuccinates, taurates, betaines, alkanolamides, alkylpolyglycosides and ethoxylated materials of the above exemplified materials, cationic material (usually polymers) such as those exemplified in U.S. Pat. No. 5,057,311 particularly exemplified at column 2, line 49 to column 7, line 23, are hereinafter incorporated by reference. These surfactants can be utilized in any of the above identified formulations at a range of about 0.01 to about 90 wt % of the compositions. The cationic species particularly the polymers are preferably incorporated at the lower portion of the range, about 0.01 to about 2.0 wt % preferably about 0.02 to 1 wt % while the other surfactants are incorporated at levels of about 2 to 90 wt %, preferably 4 to 80 wt %. The exact wt % depends upon the specific use, i.e. skin cleanser, hair cleanser etc. and the desired effect and advantages.

Examples of colorants which can be employed to provide the desired color to the composition includes reds, greens, blues, yellows, and the like all of which are approved by a local regulatory body. Examples of such color are D&C Green 8, FD&C Green 3, Ultramarine Blue, FD&C Yellow 5, FD&C Yellow 6, FD&C Blue 1, D&C Red 33, titanium dioxide and the like.

Examples of preservatives which can be employed include formalin, the alkyl parabens, phenoxyethanol, imidazolinyl area, diazidyl urea, dimethyhydantoin and the like.

Examples of chelating agents and antioxidants which inhibit the effects of free radical reactions in the composition include butylated hydroxy toluene, ethylene diamine tetracetic and (EDTA) and its salts, phosphate and others salts and acids such as ethane-1-hydroxy-1,1-diphosphonic acid, (EHDP).

Examples of antibacterial agents which can be employed in the compositions include chloro oxylene halogenated carbanilides such as Trichocarban, halogenated hydroxy diphenyl ethers such as Triclosan, and the like. Emollients include hydrocarbon oils and waxes, silicone oils, triglyceride esters, alkyl or alkenyl esters of fatty acids, fatty acids, fatty alcohols and the like.

We claim:

1. A compound of the formula $$ROCH_2CHOHCH_2O\ CH_2CH_2SO_3^-X^+$$

wherein R is alkyl or alkenyl of eight to twenty two carbon atoms or mixtures thereof inclusive and X is an alkali metal, alkaline earth metal, ammonium or substituted ammonium compound.

2. The compound in accordance with claim 1 wherein R is 10 to 20 carbon atoms and X is selected from the group consisting of sodium, potassium, ammonium or substituted ammonium.

3. The compound in accordance with claim 2 wherein R is alkyl and X is sodium or substituted ammonium.

4. The compound in accordance with claim 3 wherein R is normal and X is sodium.

5. A cleansing composition comprising a cleansing effective amount of a compound of claim 1.

6. The cleansing composition in accordance with claim 5 wherein the composition additionally has present an effective amount of at least one of a component selected from soap, synthetic surfactant, colorant, preservative, fragrance, chelating agent, antibacterial agent, emollient or a mixture thereof.

7. The composition in accordance with claim 6 wherein the component is a soap or a synthetic surfactant.

8. The composition in accordance with claim 6 wherein the component is a fragrance.

9. The composition in accordance with claim 6 wherein the component is an emollient.

10. The composition in accordance with claim 6 wherein the component is a synthetic surfactant and is selected from the group consisting of an anionic, cationic and nonionic surfactant.

* * * * *